United States Patent [19]
Park et al.

[11] Patent Number: 6,028,232
[45] Date of Patent: Feb. 22, 2000

[54] PARA-CHLORINATION OF AROMATIC COMPOUND

[75] Inventors: Sang Eon Park; Jung Whan Yoo; Poong Man Lee, all of Daejeon, Rep. of Korea

[73] Assignee: Korea Research Institute of Chemical Technology, Daejeon, Rep. of Korea

[21] Appl. No.: 08/860,711

[22] PCT Filed: Nov. 23, 1996

[86] PCT No.: PCT/KR96/00213

§ 371 Date: Sep. 23, 1997

§ 102(e) Date: Sep. 23, 1997

[87] PCT Pub. No.: WO97/18893

PCT Pub. Date: May 29, 1997

[30] Foreign Application Priority Data

Nov. 24, 1995 [KR] Rep. of Korea ............... 95-44527

[51] Int. Cl.[7] ........................................... C07C 17/00
[52] U.S. Cl. ..................... 570/210; 570/207; 570/208; 502/64; 502/65; 502/73; 502/74
[58] Field of Search .................... 570/207, 208, 570/210; 502/60, 65, 64, 73, 74

[56] References Cited

U.S. PATENT DOCUMENTS

| | | |
|---|---|---|
| 3,029,296 | 4/1962 | White et al. . |
| 3,636,171 | 1/1972 | Krumel et al. . |
| 4,235,825 | 11/1980 | Milam . |
| 4,444,583 | 4/1984 | Meyer et al. . |
| 4,724,269 | 2/1988 | Suzuki et al. ................ 570/208 |
| 4,777,305 | 10/1988 | Cobb et al. . |
| 4,835,327 | 5/1989 | Milam et al. . |
| 5,053,565 | 10/1991 | Botta et al. . |

FOREIGN PATENT DOCUMENTS

| | | |
|---|---|---|
| 0 195 514 | 9/1986 | European Pat. Off. . |
| 0 248 931 | 12/1987 | European Pat. Off. . |

OTHER PUBLICATIONS

Tetrahedron Letters, vol. 21, 3809–3812 (1980).

Chem. Letters, 1881–1182 (1992).

*Primary Examiner*—Thomas Dunn
*Attorney, Agent, or Firm*—Ladas & Parry

[57] ABSTRACT

The present invention relates to a catalyst for preparing para-chloro aromatic compounds by the liquid-phase chlorination method. The catalyst is prepared by loading transition metal salts, rare earth metal salts or a mixture thereof, and alkali metal or alkaline earth metal chlorides having a melting point of 300° C. or more, by solid-state method or impregnation method, into zeolite L being ion-exchanged by alkali metal. The present invention also relates to a process for preparing para-isomers of the chlorinated compounds by using the catalyst.

20 Claims, No Drawings

PARA-CHLORINATION OF AROMATIC COMPOUND

This application is a U.S. national-phase application based on PCT International Application No. PCT/KR96/00213, which designated the United States and which has an international filing date of Nov. 23, 1996.

TECHNICAL FIELD

The present invention relates to a catalyst for liquid-phase para-selective chlorination of aromatic compounds. The catalyst is prepared by loading transition metal salts, rare earth metal salts or mixture thereof, and alkali metal or alkaline earth metal chlorides having a melting point of 300° C. or more, into zeolite L being ion-exchanged with alkali metal, by a solid-state method or an impregnation method. The present invention also relates to a process for preparing a para-chlorinated isomer of aromatic compounds by using this catalyst.

BACKGROUND OF ART

In general, "solid-phase method" means a method for preparing a catalyst by grinding and mixing a carrier and catalyst, and then calcining this mixture. "Impregnation method" means a method for preparing a catalyst by dipping a carrier into a catalyst solution.

Chlorobenzene derivatives are widely used as a starting material or an intermediate of medicine, of agrochemistry, and in the field of organic synthesis. Up to now, they have been prepared by using Lewis acid catalysts such as ferric trichloride and antimony chloride in a liquid phase.

Dichlorobenzene derivatives produced by liquid-phase chlorination include 1,2-dichlorobenzene derivatives (o-isomer), 1,3-dichlorobenzene derivatives (m-isomer), 1,4-dichlorobenzene derivatives (p-isomer). When monochlorobenzene is chlorinated by using a Lewis acid catalyst in a liquid-phase, the proportion of isomer of dichlorobenzene is as follows;

| | |
|---|---|
| o-dichlorobenzene | 30–40% |
| m-dichlorobenzene | 0–5% |
| p-dichlorobenzene | 60–70% |

A p-isomer of chlorobenzene derivatives is widely used as an important raw material and intermediate.

U.S. Pat. No. 3,029,296 and U.S. Pat. No. 3,636,171 describe, as an example of liquid-phase chlorination in the presence of a Lewis acid, a liquid-phase chlorination process for preparing dichlorobenzene by chlorinating benzene or monochlorobenzene in the presence of ferric chloride, aluminum trichloride, tin tetrachloride or titanium tetrachloride. In the above process, the ratio of para-isomer to ortho-isomer of dichlorobenzene obtained in the presence of catalyst having a mixture of aluminum trichloride and tin tetrachloride (ratio, 1:9) is 2.7 to 3.

A process of chlorination of an aromatic compound in a liquid-phase in the presence of catalyst containing cocatalyst is described in U.S. Pat. No. 4,444,583 and U.S. Pat. No. 4,235,825.

A Lewis acid catalyst has relatively high activity. However, a Lewis acid has a disadvantage in that it can not be recycled due to its dissolution into reactive solution; and thus it may cause an environmental pollution.

In order to overcome this disadvantage, a chlorination process employing a solid-acid zeolite as a heterogeneous catalyst has been tried since 1980.

An article in *Tetrahendron Letters*, 21, 3809 (1980) reports that benzene is chlorinated by employing catalysts of solid-acid-zeolite catalysts such as ZSM-5, ZSM-11, mordenite, L and Y; and among them, zeolite catalyst L has a high selectivity of para-dichlorobenzene.

U.S. Pat. No. 4,835,327 and U.S. Pat. No. 4,777,305 describe that a high selectivity of para-dichlorobenzene is obtained by chlorinating benzene with several types of ion-exchanged zeolite L, and that in the case of chlorination in the presence of a catalyst produced by employing multivalent metals such as nickel and lanthanum, catalytic activity and selectivity of dichlorobenzene are slightly reduced relative to zeolite itself.

Nakamura et al, *Chem. Lett.*, 1881 (1992) studied a liquid-phase chlorination of benzene using many kinds of solvents in the presence of zeolite L, and obtained the result that the highest para-selectivity is shown by chlorinating benzene with dichloroethane as a solvent at the temperature of 70° C. in the presence of oxygen, and that oxygen gas accelerates para-selectivity in a liquid-phase chlorination of benzene.

EP 0,195,514 teaches that when impregnating an alkaline earth metal chloride (such as calcium chloride, strontium chloride and barium chloride) into NaY zeolite, potassium chloride and cesium chloride reduce both the conversion of monochlorobenzene and the para-selectivity of dichlorobenzene, while barium chloride slightly increases both the conversion and the selectivity.

The conversion rate of monochlorobenzene is increased by 4 wt % by zeolite KL, and para-selectivity of dichlorobenzene is rather reduced when using a zeolite catalyst in which 10 wt % of +3 valent-lanthanum salt is supported on zeolite KL.

OBJECTS OF THE INVENTION

It is the object of the invention to provide a catalyst for para-selective liquid phase chlorination of aromatic compounds, wherein alkali metal ion-exchanged zeolite L is loaded with transition metal salts, rare earth metal salts or a mixture thereof, and alkali metal or alkaline earth metal chlorides having a melting point of 300° C. or more, by a solid-state method or an impregnation method.

It is another object of the present invention to provide a process for preparing a para-isomer of a chlorinated aromatic compound by using the above catalyst.

Other objects and advantages will be apparent to those of ordinary skill in the art from the following descriptions.

DISCLOSURE OF THE INVENTION

The catalyst according to the present invention is prepared by an ion-exchange of zeolite L with alkali metal, and then loading a transitional metal salt, rare earth metal salt or mixture thereof, and alkali metal, alkaline earth metal chloride having melting point of 300° C. or more, by a solid-state method or an impregnation method.

It has been found that the conversion rate and the molar ratio of para/ortho-isomer of the aromatic compound obtained by a liquid-phase chlorination using the catalyst of the present invention are significantly higher than those of the zeolite L ion-exchanged with alkali metal.

Accordingly, the present invention provides a catalyst for a para-selective liquid-phase chlorination of an aromatic compound, in which a transitional metal salt, rare earth metal salt or a mixture of them, and an alkali metal or an alkaline earth metal chloride are loaded into zeolite L ion-exchanged with alkali metal by a solid-state method or an impregnation method.

A transitional metal salt or a rare earth metal salt and alkaline earth metal chloride can be loaded into zeolite L by an impregnation method. Alternatively, a transitional metal salt or a rare earth metal salt, an alkali metal, and an alkaline earth metal chloride may be ground together; and the mixture can be loaded into zeolite L by a solid-phase method.

Also, a transitional metal salt or a rare earth metal salt can be loaded into zeolite L by a solid-state method, and an alkali metal or an alkaline earth metal chloride can be loaded into the zeolite L by an impregnation method and vice versa. In the solid-phase method, it is preferable to heat them in an electric furnace or with an electromagnetic wave in a calcination process. Alkali metal which is ion-exchanged on zeolite L, for example, includes Li, Na, K, Cs, etc.

Said alkali metal chloride, for example, includes LiCl, NaCl, KCl, MgCl$_2$ or CaCl$_2$.

Melting Point of Metal Chloride

| Compound | Melting Point ° C. |
|---|---|
| LiCl | 605 |
| NaCl | 801 |
| KCl | 770 |
| MgCl$_2$.6H$_2$O | 714 |
| CaCl$_2$ | 782 |

The amount of transitional metal salt or rare earth metal salt and metal chloride loaded into the ion-exchanged zeolite is preferably 0.01 to 10 wt %.

Further, the present invention provides also a process for preparing a para-chloro aromatic compound by chlorinating an aromatic compound selectively to para-position in a liquid-phase by using the catalyst according to the present invention. The process may be carried out in a solvent. The solvent, for example, includes 1,2-dichloroethane, dichloromethane, carbon tetrachloride, acetic acid monochloride or ether.

A liquid-phase chlorination of an aromatic compound in the presence of a zeolite L containing alkali metal, alkaline earth metal, rare earth metal or transitional metal salts in the prior art is excellent in only one of the conversion rate and the para/ortho-molar ratio of the isomers, in relation to those of a zeolite catalyst which does not contain metal salt.

However, when the catalyst according to the present invention is used for chlorination, the conversion rate as well as the para/ortho molar ratio are significantly increased by loading multi-valent metal in various of methods, and then loading metal chloride additionally.

According to the present invention, the micropores of channel structure-typed zeolite L have a cylindrical structure consisting of 12 silicon and aluminum regular tetrahedrons. The pore size of zeolite KL is 7.1 in both the width and length. The ratio of silica to alumina of zeolite L used in the present invention is preferably 4 to 8.

Zeolite L is modified with a multi-valent metal salt by a solid-state method or an impregnation method employing an electromagnetic wave or an electrical furnace. In a solid-state method, the catalyst is produced by adding into a mortar metal salt and channel structure-type zeolite L dried at a temperature of 300° C. for 3 hours in a suitable rate, grinding the mixture thereof sufficiently, and calcining the mixture at a temperature of 500° C. Then the calcined mixture is ion-exchanged. In an impregnation method, the catalyst is prepared by dissolving metal salts in an aqueous solution, adding zeolite thereinto, stirring the solution at a temperature of 70° C. for 3 to 5 hours, then drying and calcining the resulting solid in a vacuo-rotary evaporator. In an electromagnetic wave method, the Zeolite L is loaded with multi-valent metal salts in various methods; then metal chloride is added to the zeolite L loaded with multi-valent metal salts in a solid-state method.

In order to determine the activity of a catalyst prepared by the many kinds of methods according to the present invention, an aromatic compound and dried catalyst are added into a three-necked round-bottomed flask (which is equipped with a refluxing cooler, an inlet of chlorine gas, and a sample-receiving means) and are gradually heated to a reaction temperature under the flow of nitrogen gas for 30 minutes. The catalyst is calcined at the same temperature for 3 hours before being used as described above. The temperature of the reactor is maintained in the oil bath of a thermostatic chamber by a temperature control means. The reaction is carried out under the flow of chlorine gas dehydrated at a temperature of 40 to 130° C. The reaction mixture is taken up for analysis.

Unreacted chlorine gas passing the reactor and chloric acid gas produced by the reaction are neutralized by an aqueous solution of sodium hydroxide in the receptor. The resulting product is taken up, neutralized with potassium hydroxide, filtered and analyzed by an FID-gas chromatograph (by using HP 5890A, Hewlett Packard).

In the chlorination, 1,2-dichloroethane, dichloromethane, carbon tetrachloride, acetic acid monochloride, ether, and the like may be used as a cocatalyst. In addition to benzene monochloride as a reactant, benzene and toluene may be used in the chlorination.

According to the present invention, monochlorobenzene as an aromatic compound is mainly used in the experiment. Where the process of the present invention is carried out by using an aromatic compound as reactant, the conversion rate of the aromatic compound is indicated as the percent of the difference between the amount of aromatic compound before the reaction and the amount of the aromatic compound remaining in the solution of reaction product; and the selectivity of the para-chloroaromatic compound is indicated as percent of the amount of para-chloroaromatic compound in the chlorobenzene substituted with at least one chlorine ion. And the para/ortho ratio of the para-chloroaromatic compounds is indicated as a value by dividing moles of para-chloroaromatic compound by moles of ortho-chloroaromatic compound.

BEST MODE FOR CONDUCTING THE INVENTION

Now, the present invention will be described more specifically with reference to examples hereinafter, however it should be noted that the present invention is not intended to be restricted within those specific examples.

EXAMPLES 1 TO 4

The catalyst to be used in this example was prepared by adding into a mortar Cu(NO$_3$)$_2$.3H$_2$O and sodium chloride and zeolite KL (molar ratio of silica/alumina=6.1) dried at the temperature of 300° C. for 3 hours, grinding sufficiently and calcining at the temperature of 550° C. for 6 hours. The catalyst loaded with 3.0 wt % of Cu(NO$_3$)$_2$.3H$_2$O and 2.0 wt % of sodium chloride into zeolite KL is indicated hereafter as "catalyst A".

The result of chlorination of monochlorobenzene for the catalyst determined 2 hours later from the reaction is shown below in table 1.

In the case of using catalyst A, the activity was increased by 15% than that of zeolite KL support used in Comparative Example 1; and the ratio of para/ortho isomer of dichlorobenzene was 9.2, while the ratio in zeolite KL was 6.2.

In Example 2, the catalyst was prepared by the same procedure as Example 1 except for using potassium chloride instead of the sodium chloride of Example 1; and this catalyst is indicated hereafter as "catalyst B".

In Example 3, the catalyst was prepared by the same procedure as Example 1 except for supporting with $La(NO_3)_3 \cdot xH_2O$ and CsCl; and the catalyst is indicated hereafter as "catalyst C".

In Example 4, the catalyst was prepared by the same procedure as Example 1 except for supporting with 3.0 wt % of $Cu(NO_3)_2 \cdot 3H_2O$, $IrCl_3 \cdot xH_2O$ and 2.0 wt % of KCl and NaCl; and this catalyst is indicated hereafter as "catalyst D".

COMPARATIVE EXAMPLES 1 TO 3

Zeolite KL (referred to as "catalyst 1"), zeolite CsL (referred to as "catalyst 2") and zeolite LiL (referred to as "catalyst 3") were used in chlorination of monochlorobenzene to evaluate the catalysts prepared in the examples. The result is shown below in table 1.

EXAMPLES 5 TO 7

In Example 5, the catalyst was prepared by the same procedure as Example 1 except for loading with 3 wt % of $Ce(CH_3COO)_3 \cdot 5H_2O$ in an impregnation method and additionally adding 2 wt % of LiCl thereto; and the catalyst is indicated hereafter as "catalyst E".

In Example 6, the catalyst was prepared by the same procedure as Example 5 except for using zeolite KL, $IrCl_3 \cdot xH_2O$ and $CaCl_2$ instead of CsL, $Ce(CH_3COO)_3 \cdot 5H_2O$ and LiCl, respectively; and the catalyst is indicated hereafter as "catalyst F".

In Example 7, the catalyst was prepared by the same procedure as Example 1 except for loading with 2 wt % of $Ce(CH_3COO)_3 \cdot 5H_2O$ and $CoCO_3$ in an impregnation method, calcining it and loading 5 wt % of CsCl thereto; and the catalyst is indicated hereafter as "catalyst G".

EXAMPLES 8 AND 9

In Example 8, the catalyst was prepared by the same procedure as Example 1 except for sufficiently mixing zeolite NaL and 5 wt % of $CoCO_3$, applying a uniform electromagnetic wave thereto for 5 to 30 minutes, calcining it and adding 3 wt % of KCl thereto; and the catalyst is indicated hereafter as "catalyst H".

In Example 9, the catalyst was prepared by the same procedure as Example 1 except for loading a mixture of 2 wt % of $IrCl_3 \cdot xH_2O$ and 3 wt % of $La(NO_3)_3 \cdot xH_2O$ with an electromagnetic wave and adding 5 wt % of KCl thereto; and the catalyst is indicated hereafter as "catalyst I".

COMPARATIVE EXAMPLE 4

Zeolite NaL (refer to "catalyst 4") was used in chlorination of monochlorobenzene to evaluate the catalysts prepared in the examples. The result is shown below in table 1.

EXAMPLES 10 AND 11

In Example 10, the catalyst was prepared by the same procedure as Example 1 except for adding 50 ml of 1,2-dichloroethane as cocatalyst to the catalyst obtained in Example 2; and this catalyst is indicated hereafter as "catalyst J".

In Example 11, the catalyst was prepared by the same procedure as Example 1 except for adding 5 to 10 ml of dichloromethane as cocatalyst to the catalyst obtained in Example 2; and this catalyst is indicated hereafter as "catalyst K".

COMPARATIVE EXAMPLES 5 AND 6

Zeolite KL (referred to as "catalyst 5") and 5 to 10 ml of dichloroethane were used in chlorination of monochlorobenzene to evaluate the catalysts prepared in the examples. The result is shown below in table 1.

EXAMPLES 12 AND 13

In Example 12, benzene was chlorinated by using catalyst A obtained in Example 1.

In Example 13, toluene was chlorinated by using catalyst B obtained in Example 2.

COMPARATIVE EXAMPLES 7 AND 8

In Comparative Example 7, benzene was chlorinated by using the catalyst obtained in Comparative Example 1.

In Comparative Example 8, toluene was chlorinated by using the catalyst obtained in Comparative Example 2.

TABLE 1

(Data of Liquid-Phase Chlorination of Aromatic Compounds Using Zeolite L Catalyst Modified with Multi-Valent Metal Salt, Alkali Metal and Alkaline Earth Metal Chloride)

| No. | Cat* | Reactants | Conversion Rate of Aromatic Compound (%) | Para/Ortho Molar Ratio of Aromatic Compound |
|---|---|---|---|---|
| Ex. 1 | A | MCB** | 92.5 | 12.2 |
| Ex. 2 | B | MCB | 90.8 | 9.1 |
| Ex. 3 | C | MCB | 87.3 | 9.2 |
| Ex. 4 | D | MCB | 88.2 | 9.2 |
| Ex. 5 | E | MCB | 85.2 | 7.8 |
| Ex. 6 | F | MCB | 88.5 | 8.2 |
| Ex. 7 | G | MCB | 87.8 | 7.8 |
| Ex. 8 | H | MCB | 89.5 | 9.0 |
| Ex. 9 | I | MCB | 93.2 | 8.9 |
| Ex. 10 | J | MCB | 72.4 | 52.5 |
| Ex. 11 | K | MCB | 64.4 | 37.5 |
| Ex. 12 | A | benzene | 32.5 | 7.4 |
| Ex. 13 | B | toluene | 94.7 | 2.2 |
| C. Ex. 1 | 1 | MCB | 77.1 | 6.2 |
| C. Ex. 2 | 2 | MCB | 75.2 | 6.5 |
| C. Ex. 3 | 3 | MCB | 70.8 | 6.1 |
| C. Ex. 4 | 4 | MCB | 74.5 | 6.3 |
| C. Ex. 5 | 5 | MCB | 56.4 | 19.8 |
| C. Ex. 6 | 6 | MCB | 42.9 | 18.2 |
| C. Ex. 7 | 1 | benzene | 28.4 | 6.5 |
| C. Ex. 8 | 2 | toluene | 87.5 | 1.8 | note:
*cat. = catalyst
**MCB = monochlorobenzene

What is claimed:

1. A catalyst for liquid-phase para-selective chlorination of an aromatic compound, the catalyst comprising zeolite L that is ion-exchanged with alkali metal, wherein the zeolite L is loaded by a solid-state method or an impregnation method with: (1) a transition metal salt, a rare earth metal salt, or a mixture thereof; and (2) an alkali metal chloride or alkaline earth metal chloride having a melting point of 300° C. or more.

2. A catalyst according to claim 1, wherein a calcination procedure of the solid-state method is carried out by heating with an electric furnace or an electromagnetic wave.

3. A catalyst according to claim 1, wherein the alkali metal that is ion-exchanged on the zeolite L is Li, Na, K or Cs.

4. A catalyst according to claim 1, wherein the chloride is LiCl, NaCl, KCl, $MgCl_2$ or $CaCl_2$.

5. A catalyst according to claim 1, wherein the amount of metal salt and metal chloride loaded into the zeolite L is between 0.01 and 10 wt %.

6. A process for preparing a para-chloro aromatic compound by employing the catalyst claimed in claim 1 in a liquid-phase para-selective chlorination of an aromatic compound in a solvent comprising 1,2-dichloroethane, dichloromethane, acetic acid monochloride or ether.

7. A process for preparing a para-chloro aromatic compound by employing the catalyst claimed in claim 1 in a liquid-phase para-selective chlorination of an aromatic compound in a solvent, wherein the solvent is a cocatalyst.

8. A process as claimed in claim 7, wherein the solvent comprises 1,2-dichloroethane, dichloromethane, or acetic acid monochloride.

9. A process as claimed in claim 7, wherein the solvent comprises 1,2-dichloroethane.

10. A process as claimed in claim 7, wherein the aromatic compound comprises benzene monochloride, benzene, or toluene.

11. A catalyst for liquid-phase para-selective chlorination of an aromatic compound, the catalyst comprising zeolite L that is ion-exchanged with alkali metal, wherein the zeolite L is loaded with: (1) a transition metal salt, a rare earth metal salt, or a mixture thereof; and (2) an alkali metal chloride or alkaline earth metal chloride having a melting point of 300° C. or more.

12. A catalyst according to claim 11, wherein the alkali metal that is ion-exchanged on the zeolite L is Li, Na, K or Cs.

13. A catalyst according to claim 11, wherein the chloride is LiCl, NaCl, KCl, $MgCl_2$ or $CaCl_2$.

14. A catalyst according to claim 11, wherein the amount of metal salt and metal chloride loaded into the zeolite L is between 0.01 and 10 wt %.

15. A process for preparing a para-chloro aromatic compound by employing the catalyst claimed in claim 11 in a liquid-phase para-selective chlorination of an aromatic compound in a solvent comprising 1,2-dichloroethane, dichloromethane, acetic acid monochloride, or ether.

16. A process for preparing a para-chloro aromatic compound by employing the catalyst claimed in claim 11 in a liquid-phase para-selective chlorination of an aromatic compound in a solvent, wherein the solvent is a cocatalyst.

17. A process as claimed in claim 16, wherein the solvent comprises 1,2-dichloroethane, dichloromethane, or acetic acid monochloride, or ether.

18. A process as claimed in claim 16, wherein the solvent comprises 1,2-dichloroethane.

19. A process as claimed in claim 16, wherein the aromatic compound comprises benzene monochloride, benzene, or toluene.

20. A catalyst according to claim 12, wherein the chloride is LiCl, NaCl, KCl, $MgCl_2$ or $CaCl_2$, and wherein the amount of metal salt and metal chloride loaded into the zeolite L is between 0.01 and 10 wt %.

* * * * *